United States Patent
Tiemann et al.

(10) Patent No.: US 10,926,239 B2
(45) Date of Patent: Feb. 23, 2021

(54) FUEL PROCESSOR COMPONENT FOR A PROPYLENE GLYCOL FUEL PROCESSOR AND PROPYLENE GLYCOL FUEL PROCESSOR

(71) Applicant: DIEHL AEROSPACE GMBH, Ueberlingen (DE)

(72) Inventors: David Tiemann, Gau-Odernheim (DE); Jochen Schuerer, Gau-Bischofsheim (DE); Gunther Kolb, Neustadt/W. (DE)

(73) Assignee: DIEHL AEROSPACE GMBH, Ueberlingen (DE)

( * ) Notice: Subject to any disclaimer, the term of this patent is extended or adjusted under 35 U.S.C. 154(b) by 84 days.

(21) Appl. No.: 15/899,667

(22) Filed: Feb. 20, 2018

(65) Prior Publication Data
US 2018/0236431 A1    Aug. 23, 2018

(30) Foreign Application Priority Data
Feb. 20, 2017   (DE) .......................... 102017001562.7

(51) Int. Cl.
*B01J 19/00*      (2006.01)
*B01J 19/24*      (2006.01)
(Continued)

(52) U.S. Cl.
CPC ......... *B01J 19/249* (2013.01); *B01J 19/0013* (2013.01); *B01J 19/0093* (2013.01);
(Continued)

(58) Field of Classification Search
CPC .......... B01F 2215/00; B01F 2215/0001; B01F 2215/0098; B01J 19/0013; B01J 19/0093; B01J 19/24; B01J 19/249; B01J 2208/00; B01J 2208/00008; B01J 2208/00628; B01J 2208/00716; B01J 2219/00; B01J 2219/00781; B01J 2219/00783;
(Continued)

(56) References Cited

U.S. PATENT DOCUMENTS 5,811,062 A      9/1998   Wegeng et al.
8,497,308 B2 *   7/2013   Tonkovich ............. C10G 2/341
                                                        518/700

(Continued)

OTHER PUBLICATIONS

D'Connell, M., "A Review of Current Microchannel Based Fuel Processing Systems With a Focus on the Prime Development Issues for Early Market Implementation", 4th World Hydrogen Technologies Convention, 2011, Glasgow, U.K.

*Primary Examiner* — Natasha E Young

(57) ABSTRACT

The invention relates to a fuel processor component for a propylene glycol fuel processor, comprising at least one housing (G) having at least two inlets (E1, E2) and two outlets (A1, A2),
wherein there is a multitude of first plates (P1) having a first side (S1) and a second side (S2) and second plates (P2) having a third side (S3) and a fourth side (S4) arranged as a stack in the housing (G),
wherein the stacked first and second plates (P1, P2) form at least first cavities (H1) and second cavities (H2), wherein the first inlet (E1) has fluid connection to the first outlet (A1) via first cavities (H1) and the second inlet (E2) has fluid connection to the second outlet (A2) via second cavities (H2).
The invention further relates to a propylene glycol fuel processor.

17 Claims, 9 Drawing Sheets

Figure 1:
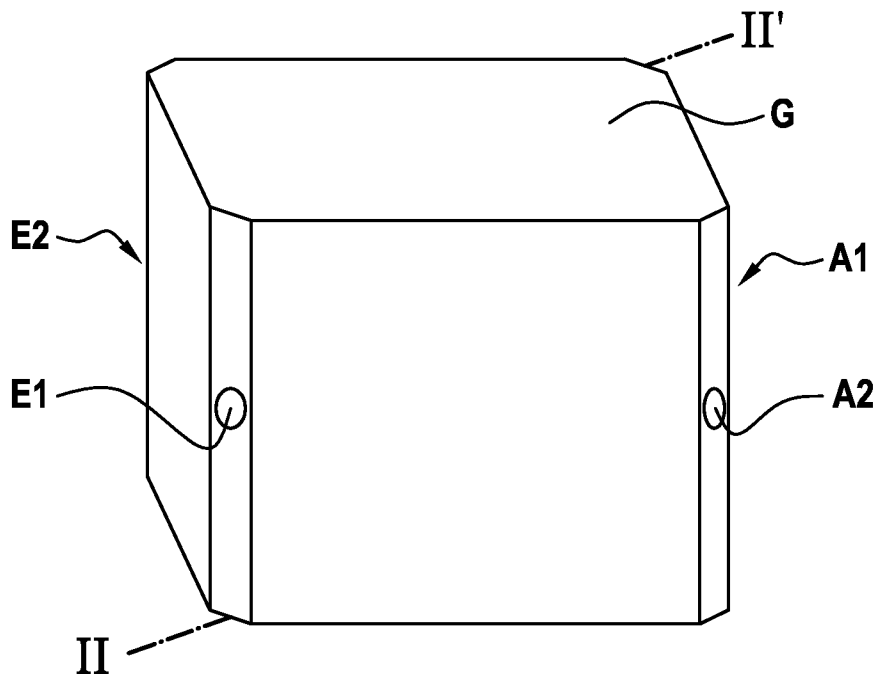

(51) Int. Cl.
<table>
<tr><td>C07C 31/00</td><td>(2006.01)</td></tr>
<tr><td>C07C 31/20</td><td>(2006.01)</td></tr>
<tr><td>H01M 8/00</td><td>(2016.01)</td></tr>
<tr><td>H01M 8/06</td><td>(2016.01)</td></tr>
<tr><td>C10K 3/00</td><td>(2006.01)</td></tr>
<tr><td>C10K 3/04</td><td>(2006.01)</td></tr>
<tr><td>C10L 1/00</td><td>(2006.01)</td></tr>
<tr><td>C10L 1/02</td><td>(2006.01)</td></tr>
<tr><td>H01M 8/0612</td><td>(2016.01)</td></tr>
<tr><td>H01M 8/0668</td><td>(2016.01)</td></tr>
</table>

(52) U.S. Cl.
CPC ............. *C07C 31/205* (2013.01); *C10K 3/04* (2013.01); *C10L 1/02* (2013.01); *H01M 8/0618* (2013.01); *B01F 2215/0098* (2013.01); *B01J 2208/00628* (2013.01); *B01J 2208/00716* (2013.01); *B01J 2219/00783* (2013.01); *B01J 2219/00835* (2013.01); *B01J 2219/00873* (2013.01); *B01J 2219/00894* (2013.01); *B01J 2219/2453* (2013.01); *B01J 2219/2458* (2013.01); *B01J 2219/2459* (2013.01); *B01J 2219/2462* (2013.01); *B01J 2219/2465* (2013.01); *B01J 2219/2477* (2013.01); *B01J 2219/2479* (2013.01); *B01J 2219/2497* (2013.01); *H01M 8/0668* (2013.01); *Y02P 20/129* (2015.11)

(58) Field of Classification Search
CPC .... B01J 2219/00819; B01J 2219/00835; B01J 2219/00873; B01J 2219/00894; B01J 2219/24; B01J 2219/2401; B01J 2219/245; B01J 2219/2451; B01J 2219/2453; B01J 2219/2456; B01J 2219/2458; B01J 2219/2459; B01J 2219/2561; B01J 2219/2462; B01J 2219/2465; B01J 2219/2476; B01J 2219/2477; B01J 2219/2479; B01J 2219/2491; B01J 2219/2497; C07C 31/00; C07C 31/18; C07C 31/20; C07C 31/205; C10K 3/00; C10K 3/02; C10K 3/04; C10L 1/00; C10L 1/02; H01M 8/00; H01M 8/06; H01M 8/0606; H01M 8/0612; H01M 8/0618; H01M 8/0662; H01M 8/0668; Y02P 20/00; Y02P 20/10; Y02P 20/12; Y02P 20/129

See application file for complete search history.

(56) References Cited

U.S. PATENT DOCUMENTS

<table>
<tr><td>2002/0131919 A1*</td><td>9/2002</td><td>DeBellis ............... B01J 19/249<br>422/600</td></tr>
<tr><td>2010/0248083 A1</td><td>9/2010</td><td>Whyatt et al.</td></tr>
<tr><td>2012/0095268 A1</td><td>4/2012</td><td>Tonkovich et al.</td></tr>
<tr><td>2012/0217441 A1</td><td>8/2012</td><td>Johnston</td></tr>
</table>

* cited by examiner

FUEL PROCESSOR COMPONENT FOR A PROPYLENE GLYCOL FUEL PROCESSOR AND PROPYLENE GLYCOL FUEL PROCESSOR

The invention relates to a fuel processor component for a propylene glycol fuel processor and to a propylene glycol fuel processor.

The prior art encompasses fuel processors for other fuels. A fuel processor of this kind for LPG, octane, kerosene and diesel is known, for example, from the publication M. O'Connel et al., $4^{th}$ World Hydrogen Technologies Convention, 2011, Glasgow, U.K. The fuel processor comprises reactors. A reactor of this kind may comprise a multitude of identical plates which, for example, are partially equipped with a catalyst.

There is a need for fuel processor components that are suitable for use with propylene glycol. There is additionally a requirement for compact fuel processors having low weight and small dimensions for use in vehicles, for example aircraft, in which available waste heat is utilized optimally.

The problem addressed by the invention is that of specifying a fuel processor component for a propylene glycol fuel processor having small dimensions, low weight and a high power density.

The problem addressed by the invention is solved by the features of claim 1. Appropriate configurations are apparent from the dependent claims.

According to the invention, a fuel processor component for a propylene glycol fuel processor is specified, comprising at least one housing having at least two inlets and two outlets,
wherein there is a multitude of first plates having a first side and a second side and second plates having a third side and a fourth side arranged as a stack in the housing.

The stacked first and second plates form at least first cavities and second cavities, wherein the first inlet has fluid connection to the first outlet via first cavities and the second inlet to the second outlet via second cavities.

The fuel processor component according to the invention is light and compact. By adjusting the sequence of the plates, it is possible to optimize the supply or removal of heat to the power range of the fuel processor component.

A fuel processor generally comprises a multitude of fuel processor components, such as a reformer, a water-gas shift reactor, what is called a PrOx reactor, an evaporator, a heat exchanger and a startup apparatus.

A liquid fuel is evaporated in an evaporator. In the case of a propylene glycol fuel processor, the fuel to be evaporated consists of a propylene glycol/water mixture. In the reformer, the fuel is converted to a hydrogenous gas and various tail gases, including carbon monoxide. In the water-gas shift reactor and in the PrOx reactor, the gases obtained in the reformer, especially the carbon monoxide obtained, are converted to carbon dioxide, such that the offgas from the PrOx reactor comprises only small proportions, if any, of carbon monoxide. A gas flows through the heat exchanger or, if appropriate, two different gases in identical or opposing directions. The heat exchanger serves to regulate the temperature of the gas before it is introduced into the downstream reactor or to remove heat of reaction from a reactor.

The fuel processor component has at least two separate gas conduits, which are firstly the first cavities with a corresponding first inlet and a first outlet, and secondly the second cavities having a second inlet and a second outlet.

The fuel processor component may be provided with a gas/liquid distributor on the inlet side and with a gas/liquid collection unit on the outlet side.

In an appropriate configuration, first and/or second plates comprise surface structuring, wherein the surface structuring comprises a pattern and/or channels, a distributor structure and a collection structure. The pattern is a regular arrangement of elevations and depressions which guide a flow from the distributor structure to the collection structure.

Such surface structuring can be introduced by a multitude of known methods, for example embossing, injection moulding, laser structuring, additive manufacturing, e.g. 3D printing, and others.

In a further preferred configuration, a first number of the first and second plates is arranged in a given sequence, wherein the first number of the first and second plates forms a repeating unit. There is thus preferably a second number of repeating units accommodated in the housing.

A fuel processor component may especially comprise 2 to 500, preferably 5 to 250, preferably 50 to 200, preferably 100 to 150, repeating units.

Preferably, the first side may have structuring configured for a gas reaction and the second side may be a cooling or evaporator side.

In a further appropriate configuration, the third side has the same surface structuring as the second side and the fourth side the same surface structuring as the first side.

In a further configuration, the fuel processor component is an evaporator, wherein at least one first side of a first plate is configured as an evaporator and a second side of the plate for passage of hot gas. Thus, the heat from the hot gas is transferred directly to the opposite side of the same plate for evaporation of the fuel. In the context of the invention, "evaporator" may also mean "superheater", and "evaporate" may also mean "superheat".

In an alternative configuration, the fuel processor component is an evaporator, wherein a first and a second side of the first plate are configured as evaporator surfaces. A third side of the second plate is configured as a hot gas side and a fourth side of the second plate is configured as a flat surface. Optionally, a fifth side of the third plate is configured as a hot gas side for passage of the hot gas or for passage of air, and a sixth side of the third plate as a flat surface. Each evaporator surface is opposite a flat surface, and two hot gas sides are opposite one another.

In this configuration, two or optionally three different gases or fluids are guided through the evaporator. A first cavity in this case is an evaporation cavity. The adjacent cavity in each case is heated by a hot gas. An evaporator of this kind may be designed as a superheater. The structuring of the third side, the hot gas side and the fifth side may be identical.

Preferably, the evaporator according to the invention has a repeating unit with the following sequence: first side, second side, fourth side, third side, third side, fourth side, first side, second side, fourth side, third side, third side, fourth side, sixth side, fifth side, fifth side, sixth side.

This sequence comprises eight plates, wherein the eight plates comprise two or three different plates.

In an alternative configuration, the fuel processor component is a heat exchanger, wherein at least one first side is configured for passage of a first gas and one second side for passage of a second gas. The first gas and second gas may be identical. However, they are guided within fluid-separated conduit pathways. Appropriately, the first gas and the second gas can be guided through the fuel processor component in the same direction or in opposing directions.

In an alternative configuration, the fuel processor component according to the invention is a water-gas shift reactor, wherein the first plate has a first side configured as a cooling plate and a second side configured as a reaction side. The water-gas shift reactor according to the invention thus has a heat exchanger integrated into the water-gas shift reactor for removal of heat of reaction. Appropriately, every sixth plate in a repeating unit has a cooling side.

A "reaction side" is understood to mean a side having a multitude of channels and/or a pattern which is configured such that a reaction proceeds. A reaction side of this kind may especially be coated with a catalyst.

The number of cooling sides is dependent on the amount of heat of reaction which arises in the reaction in the water-gas shift reactor and has to be removed.

In a further alternative configuration, the fuel processor component according to the invention is a PrOx reactor, wherein a first plate has a first side configured as a cooling side and a second side configured as a cooling side, wherein a second plate has a third side configured as a reaction side and a fourth side configured as a gas feed side, wherein a third plate has a fifth side configured as a reaction side and a sixth side configured as an unstructured surface. A "gas feed side" is understood to mean a side within which a conduit for an inflowing gas is integrated. The conduit has fluid connection to the opposite side of the plate. The aforementioned fourth side has a conduit for feeding in air, which has fluid connection to a multitude of distributor channels on the aforementioned third side. The distributor channels present in the third side are configured such that they each have at least one opening to the reaction side.

The surface configured as a cooling side may, in one configuration, have structuring for passage of a cooling gas. In a further configuration, a cooling side may be configured as an evaporator side, such that the heat of reaction generated in the PrOx reactor can be utilized for evaporating the fuel.

In an alternative configuration, the second plate may be configured as a flat surface on the fourth side.

Appropriately, a repeating unit in the PrOx reactor has the following sequence: first side, second side, sixth side, fifth side, third side, fourth side, fourth side, third side, fifth side, sixth side.

The invention additionally relates to a propylene glycol fuel processor comprising a heat exchanger and a series connection of an evaporator, a reformer, a water-gas shift reactor and a PrOx reactor. At least one of the fuel processor components is a fuel processor component configured as an evaporator in accordance with the invention, a fuel processor component configured as a heat exchanger in accordance with the invention, a fuel processor component configured as a water-gas shift reactor in accordance with the invention and/or a fuel processor component configured as a PrOx reactor in accordance with the invention. Advantageously, all the aforementioned components are configured in accordance with the invention. The propylene glycol fuel processor in this configuration comprises relatively few different plates for formation of the individual fuel processor components. The integration of a cooling or evaporator unit into the water-gas shift reactor or PrOx reactor already achieves high integration.

In an appropriate configuration of the propylene glycol fuel processor, at least two of the fuel processor components are arranged one on top of the other such that the plate stacks of the at least two fuel processor components form a superstack. A "superstack" is understood to mean a stack which is interrupted only by housing base or housing lid plates arranged between the stacks of the individual components. In a particularly integrated form, the housing lid plate of a fuel processor component arranged as the lower fuel processor component and a housing base plate of a fuel processor component arranged above it may be replaced by a single separating plate.

In a further appropriate configuration, a heat exchanger, a water-gas shift reactor and a PrOx reactor are arranged one on top of another such that the plates of the heat exchanger, water-gas shift reactor and PrOx reactor form a superstack, wherein the water-gas shift reactor is arranged in a middle region of the superstack and wherein a first gas can flow successively through the heat exchanger, the water-gas shift reactor and the PrOx reactor. The further gases provided for flow through the particular reactor can be guided only through one or more of the reactors within a fluid-separated system.

Figure 2:
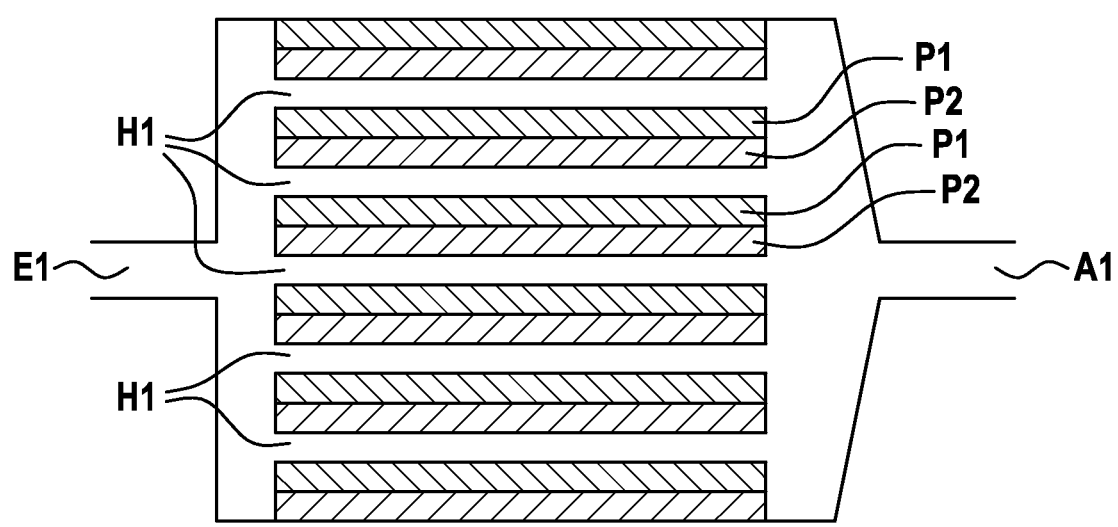
Figure 3:
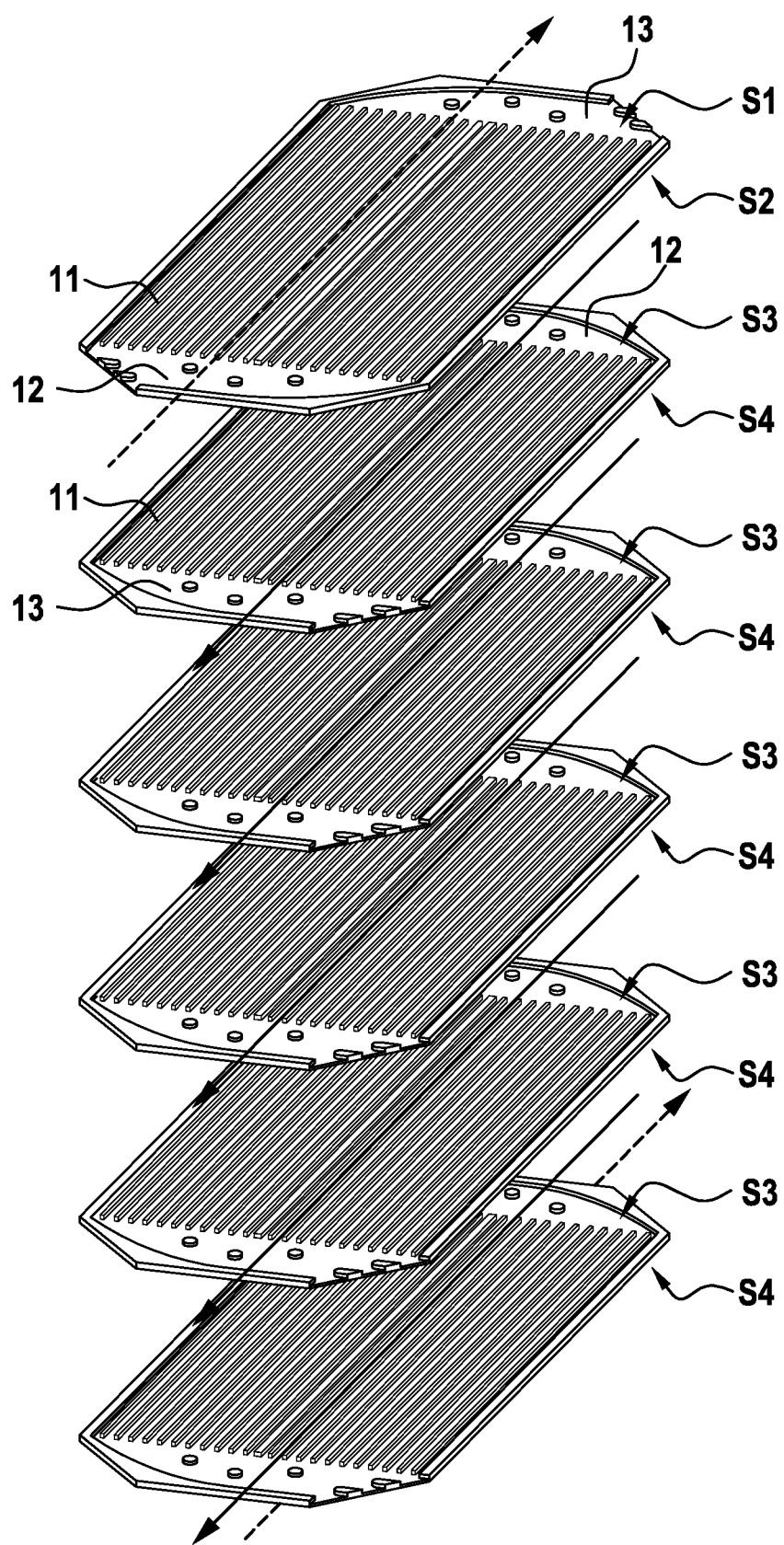
Figure 4A:
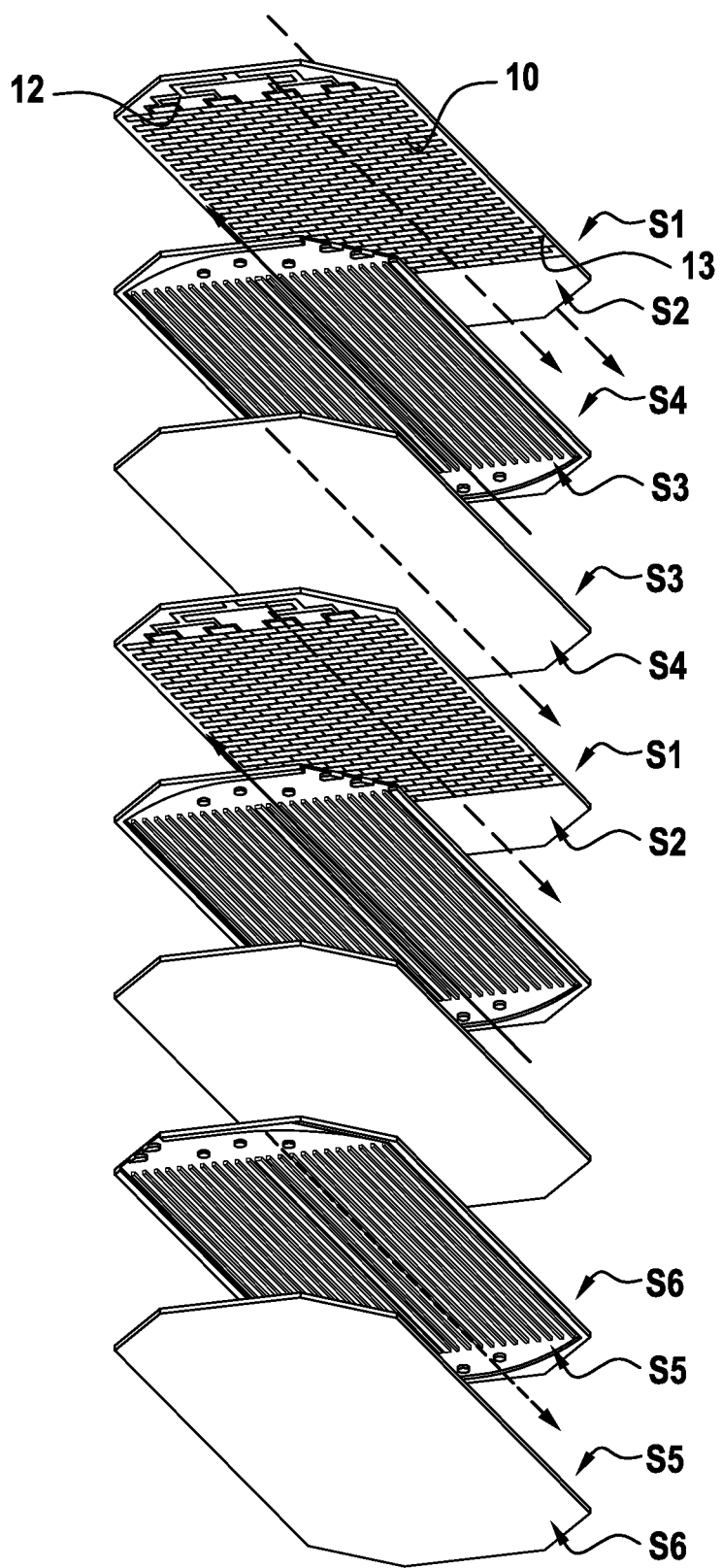
Figure 4B:
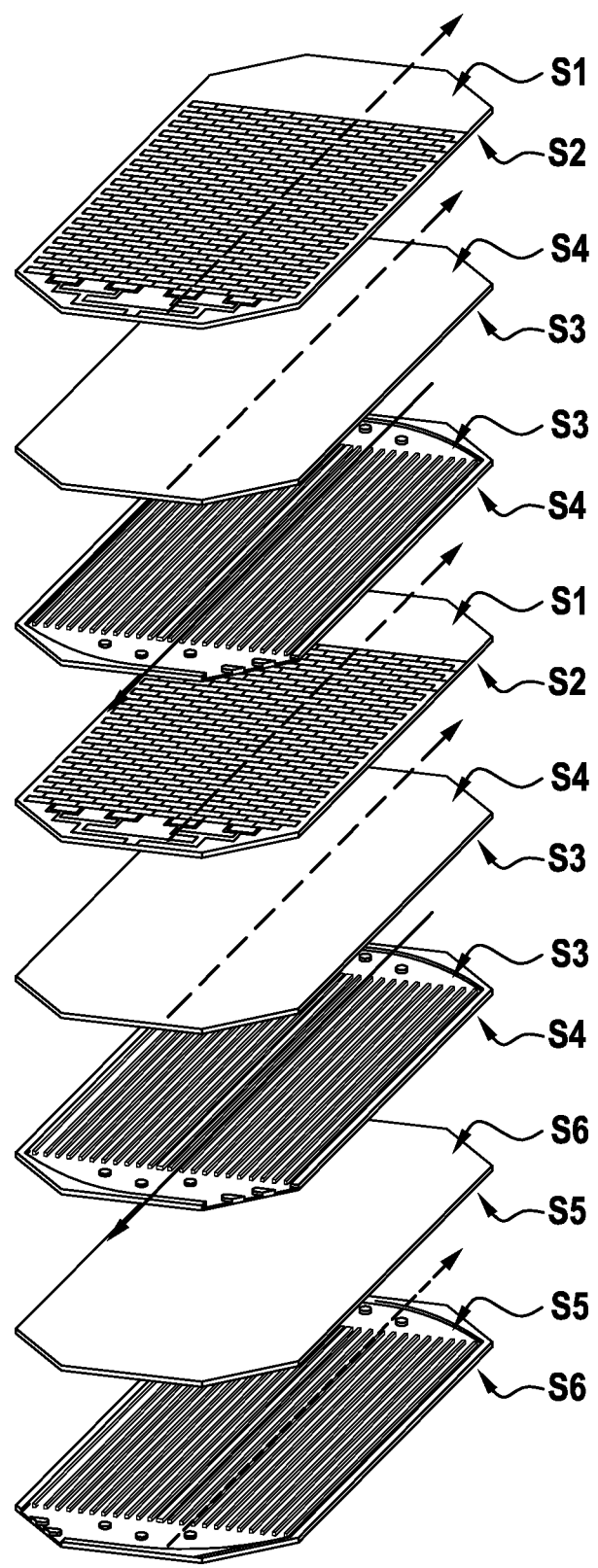
Figure 5A:
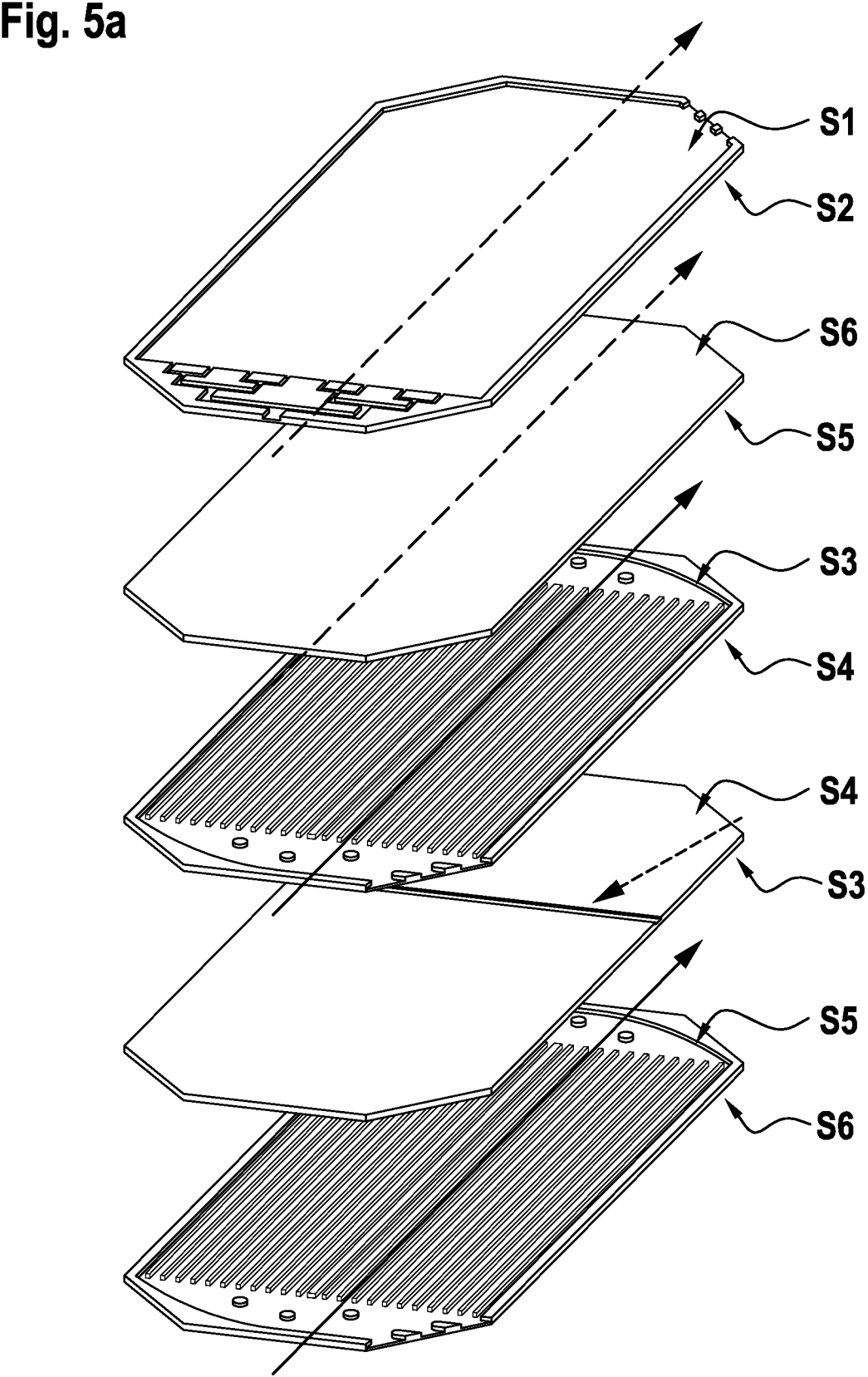
Figure 5B:
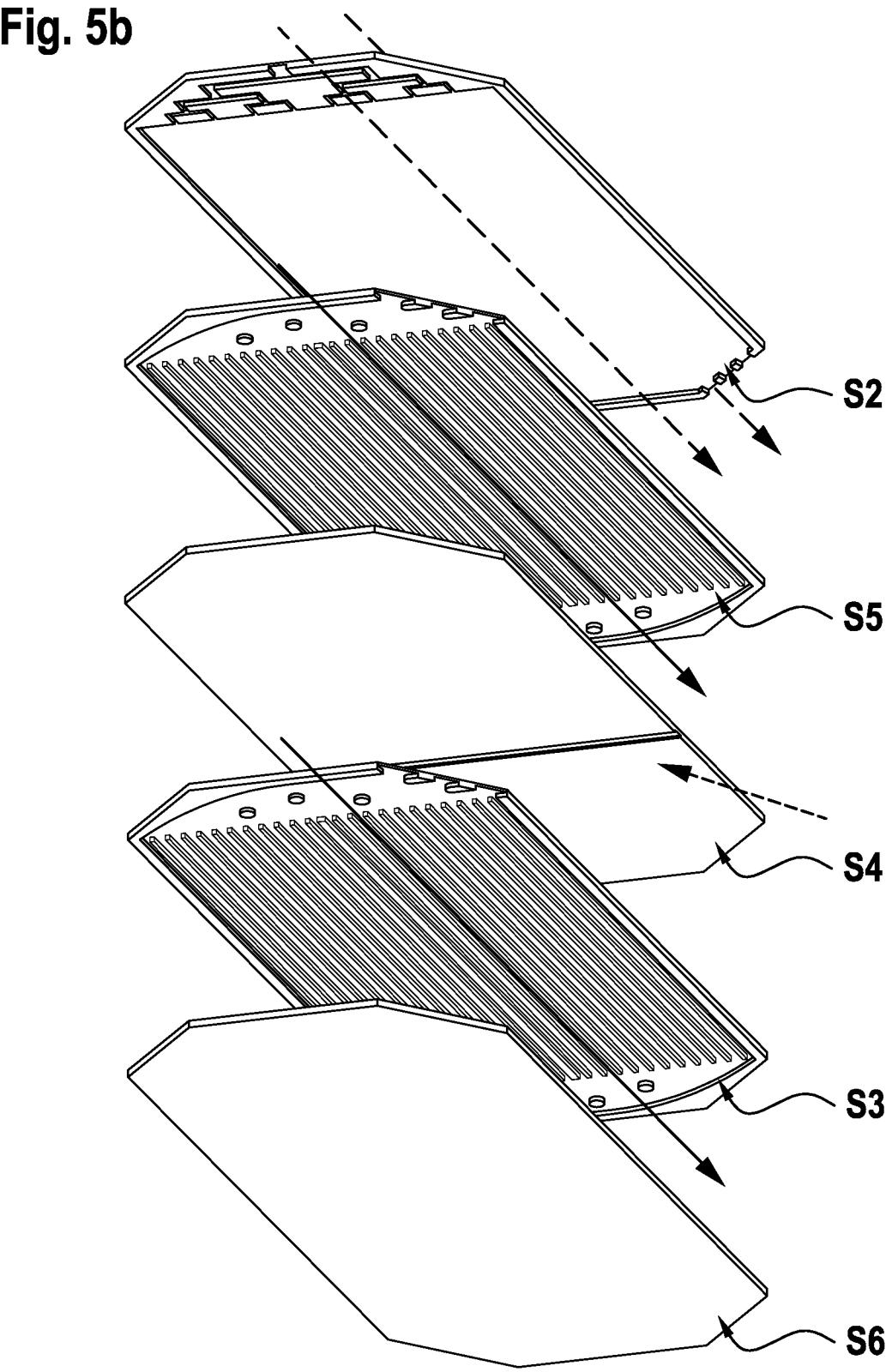
Figure 6:
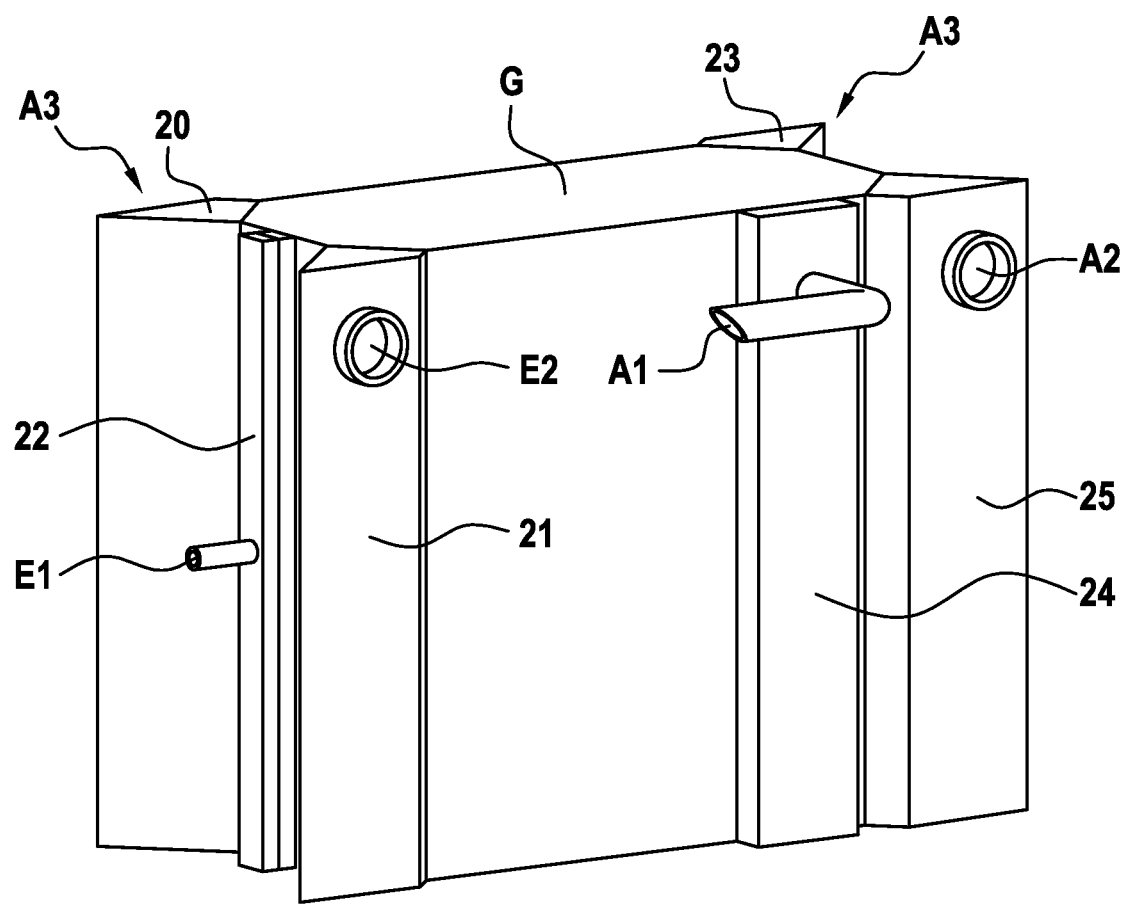
Figure 7:
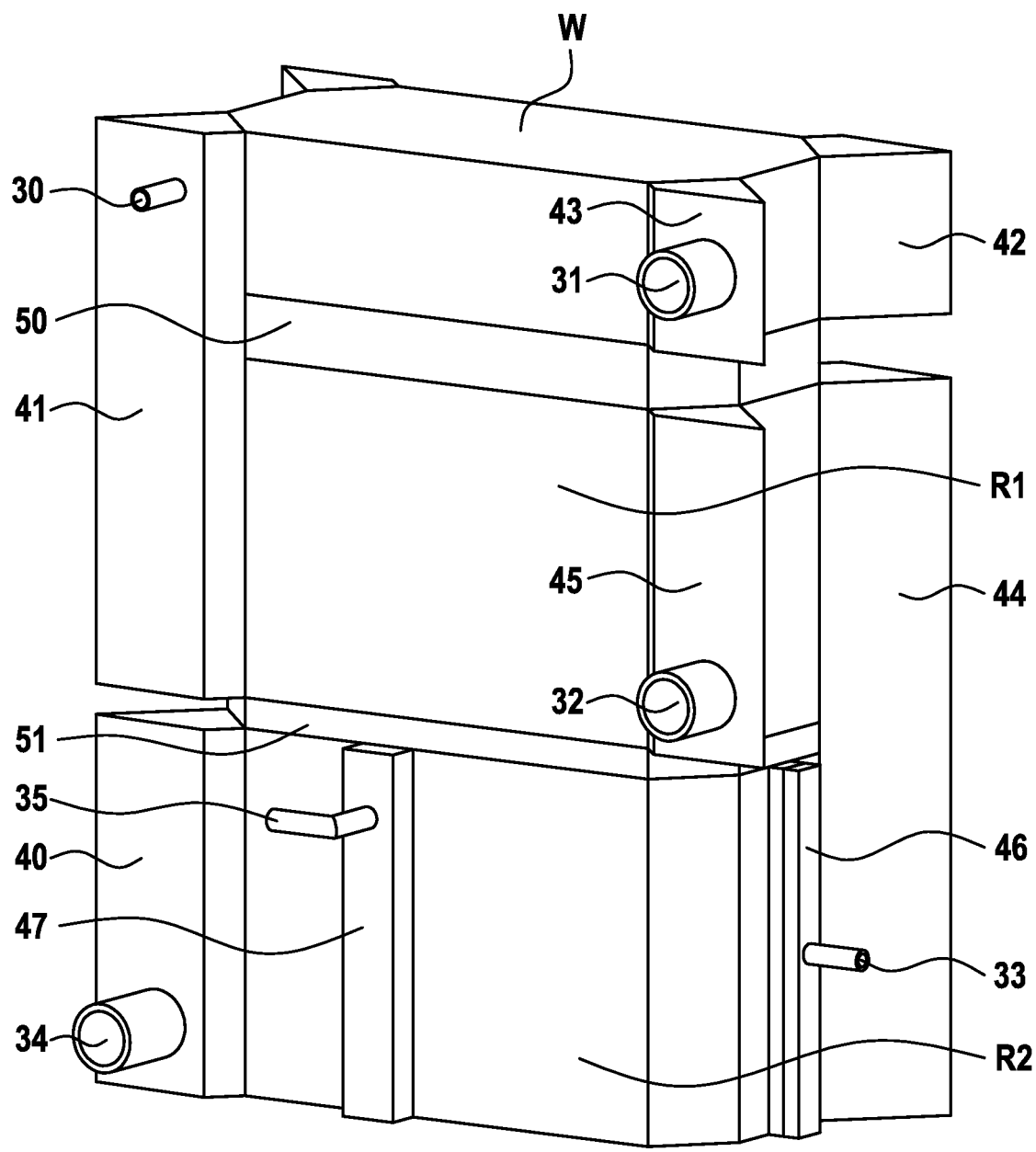
Figure 8:
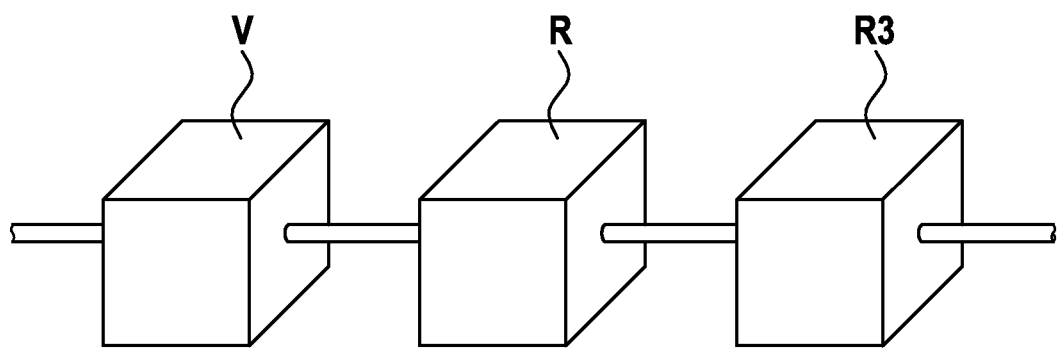

The invention is elucidated in detail hereinafter with reference to drawings. The drawings are schematic diagrams. The figures show:

FIG. 1 a schematic diagram of a fuel processor component according to the invention, FIG. 2 a cross section through the fuel processor component according to FIG. 1 along the section line II-II', FIG. 3 a plate sequence in the water-gas shift reactor, FIG. 4A, 4B a plate sequence in an evaporator, FIG. 5a, 5b a plate sequence in a PrOx reactor, FIG. 6 a schematic diagram of an evaporator, FIG. 7 a schematic diagram of a stack of a PrOx reactor, a water-gas shift reactor and an evaporator, and FIG. 8 a schematic diagram of a fuel processor according to the invention.

FIG. 1 shows the housing G of a fuel processor component having a first inlet E1, a second inlet E2, a first outlet A1 and a second outlet A2. The first inlet E1 and the second inlet E2 or the first outlet A1 and the second outlet A2 are arranged at different ends of a housing G. In this configuration, the housing G has a rectangular footprint with each of the corners bevelled, wherein the first inlet E1 and the second inlet E2 and the first outlet A1 and the second outlet A2 are arranged on a lateral face of the bevelled corner. In a configuration for three gases, it is additionally possible for a third inlet E3 and, opposite that, a third outlet A3 to be arranged on the top faces of the housing G. In this way, in the region of the plates P1, P2, P3, it is possible to achieve an identical flow direction or an opposite flow direction.

FIG. 2 shows a cross section along the section line II-II' of FIG. 1. The first inlet E1 provides fluid connection of exclusively first cavities H1. The first cavities H1 have fluid connection to the first outlet A1. In the same way, only second cavities H2 are accessible via the second inlet E2 and the second outlet A2.

FIG. 3 shows a plate sequence of a fuel processor component configured as a water-gas shift reactor R1. The plate sequence comprises plates P1, P2, P3 having a first side S1, a second side S2, a third side S3 and a fourth side S4. On the first side S1, a distributor structure 12 is accessible from a front left-hand side according to the figure; the first side S1 comprises channels 11 and a collection structure 13 which leads to a first outlet A1 on the rear right-hand side. The third side S3, by contrast, has a distributor structure 12 and channels 11 open to the left-hand rear side, and a collection structure 13 open to the right-hand front side.

The channels 11 on the first side S1, the second side S2, the third side S3 and the fourth side S4 are of identical configuration in this working example. The flow through a cooling cavity formed between a fourth side S4 and a first side S1, in the view shown in FIG. 3, is away from the observer; the flow through a reaction cavity formed by the second side S2 and the third side S3 or by the third side S3 and the fourth side S4 is toward the observer.

FIGS. 4A and 4B show a plate sequence of a fuel processor component configured as an evaporator V in an oblique view from the bottom (FIG. 4A) and in an oblique view from the top (FIG. 4B). The first side S1 and the second side S2 are configured as the evaporator side. They have a feed arranged in the middle to a distributor structure 12.

The evaporator side has been provided with a pattern 10 or channels (not shown). The distributor structure 12 is arranged centrally on one side; the collection structure 13 is arranged in a direction at right angles thereto.

The third side S3 is configured as a hot gas side, wherein the fourth side S4 on the reverse side of the third side S3 is configured as a flat surface. The fourth side S4 in this working example faces toward the second side S2 and thus forms the evaporator cavity with the second side S2.

Two third sides S3 are arranged opposite one another such that the hot gas is guided within channels 11 formed by the two third sides S3. Optionally—as shown—a third plate P3 having a fifth side S5 and a sixth side S6 is arranged, wherein the fifth side S5 is configured as a hot gas conduit for conduction of air and a sixth side S6 as a flat surface. The stack in this case has four second plates P2 and two third plates P3, wherein the second plates P2 and the third plates P3 may be identical. The stack shown, comprising the first plates P1, the second plates P2 and the third plates P3, forms a repeating unit.

FIGS. 5a and 5b show a plate sequence in a PrOx reactor R2. FIG. 5a shows an oblique view from the top; FIG. 5b shows an oblique view from the bottom. The first plate P1 having a first side S1 and a second side S2 is configured as a cooling side or as an evaporator side. When the side is configured as an evaporator side, it comprises structuring suitable for evaporation in the form of a pattern (not shown). A second plate P2 comprises a third side S3 and a fourth side S4, wherein the third side S3 is configured as a reaction side and the fourth side S4 as a flat surface or—as shown in the execution—comprises an air supply channel 14 for supply of air to the opposite side of the second plate P2. The third plate P3 comprises the fifth side S5 and the sixth side S6, wherein the sixth side S6 is configured as a flat surface and the fifth side S5 as a reaction side. The repeating unit of the plate stack in the PrOx reactor R2 accordingly consists of one first plate P1, two second plates P2 and two third plates P3, wherein a possible way of cooling the PrOx reactor R2 is an evaporation of a propylene glycol/water mixture between the first side S1 and the second side S2 of the first plate P1.

FIG. 6 shows a fuel processor component configured as an evaporator V. The evaporator V comprises a housing G having a first inlet E1, a second inlet E2 and a third inlet (not shown), and also a first outlet A1, a second outlet A2 and a third outlet A3. Especially the plate sequence according to FIG. 4A, FIG. 4B may be arranged within the housing G, wherein FIG. 4A and FIG. 4B show a repeating unit. A multitude of the repeating units according to FIG. 4A and FIG. 4B are arranged within the housing G according to FIG. 6. More particularly, an arrangement of between 2 to 500, especially 5 to 250, especially 50 to 100, repeating units is possible. Reference numerals 20, 22 and 23 identify fluid distributor units, and reference numerals 21, 24 and 25 identify fluid and especially gas collection units. A propylene glycol/water mixture is introduced through the first inlet E1, which is guided either via the fluid distributor unit 22 or via the side configured as an evaporator surface, by means of which the propylene glycol/water mixture is evaporated. The vapour thus generated is collected in the gas collection unit 24 and guided out through the first outlet A1. Air is introduced through the second inlet E2, which can be guided through the evaporator V as an alternative to the preheating of the evaporator V or to the heating of the air. The air is guided through the hot gas sides envisaged for the purpose. The gas collection unit 25 guides the air to the second outlet A2.

The third inlet E3 serves as an inlet for hot gas which can be heated in another fuel processor component, for example with heat from the reformer or another burner. The hot gas is guided to the third outlet A3 by the gas collection unit 20.

FIG. 7 shows a stack of three fuel processor components comprising a heat exchanger W, a water-gas shift reactor R1 and a PrOx reactor R2. The heat exchanger W may be designed as a countercurrent heat exchanger in which a hydrogen-containing fuel gas, reformate here, is cooled by a further gas. The inlet for the further gas is not shown. The further gas is guided to the cooling gas outlet 31 via a collection unit 43. The fuel gas, especially reformate, can be guided into the heat exchanger W via the distributor unit 42 and be discharged into a combined gas collection/gas distributor unit 41.

The fuel gas, especially reformate, is guided through the combined gas collection/gas distributor unit 41 into the water-gas shift reactor R1 and subsequently guided through a combined gas collection/gas distributor unit 44 into the PrOx reactor R2. Via the inlet 32 and the distributor unit 45, air can be guided in the water-gas shift reactor R1 into the cavities intended for cooling.

The PrOx reactor R2 comprises an inlet 33 having a distributor unit 46 for introduction of a gas, especially the fuel, for evaporative cooling, and a further inlet 35 with a distributor unit 47 connected thereto for introduction of air. The gas generated in the PrOx reactor R2 is guided through a gas collection unit 40 to an offgas outlet 34. A fuel cell may be connected to this offgas outlet 34. The vapour generated by the evaporative cooling is removed through a further outlet (not shown).

The reactor combination, shown in FIG. 7, of the three fuel processor components comprising the "CO cleanup" reactors has a particularly compact design and a high power density, since plates P1, P2, P3 of the same size are arranged in all fuel processor components, i.e. in the heat exchanger W, water-gas shift reactor R1 and PrOx reactor R2, and these are separated only by intermediate plates 50, 51 or spacers.

FIG. 8 shows a propylene glycol fuel processor comprising a fuel processor component configured as an evaporator V, a downstream reformer R and a CO cleanup reactor unit R3. The CO cleanup reactor unit R3 is composed of a heat exchanger W, a water-gas shift reactor R1 and a PrOx reactor R2. The CO cleanup reactor unit R3 is especially configured as shown in FIG. 7. The evaporator V is shown in detail in FIG. 6. The reformer R converts the evaporated propylene glycol/water mixture, especially by means of a catalyst applied within the reformer R, to a hydrogenous gas and various tail gases. In the CO cleanup reactor unit R3, the carbon monoxide content of the gas is reduced in the water-gas shift reactor R1 present therein and in the PrOx reactor R2. More particularly, the evaporator V and the CO cleanup reactor unit R3 comprise further inlets and outlets which are not shown for the sake of clarity. The connecting conduit between the evaporator V, the reformer R and the CO cleanup reactor unit R3 is the conduit for the fuel or the fuel converted by reaction.

LIST OF REFERENCE NUMERALS 10 pattern
11 channel
12 distributor structure
13 collection structure
14 air supply channel
20 distributor unit
21 collection unit
22 distributor unit
23 distributor unit
24 collection unit
25 collection unit
30 additional inlet
31 cooling outlet
32 inlet
33 evaporation gas inlet
34 offgas outlet
35 air inlet
40 gas collection unit
41 collection/distributor unit
42 distributor unit
43 collection unit
44 collection/distributor unit
45 distributor unit
46 distributor unit
47 distributor unit
50 first intermediate plate
51 second intermediate plate
A1 first outlet
A2 second outlet
A3 third outlet
E1 first inlet
E2 second inlet
E3 third inlet
G housing
H1 first cavity
H2 second cavity
P1 first plate
P2 second plate
P3 third plate
R reformer
R1 water-gas shift reactor
R2 PrOx reactor
R3 CO cleanup reactor unit
S1 first side
S2 second side
S3 third side
S4 fourth side
S5 fifth side
S6 sixth side
V evaporator
W heat exchanger

The invention claimed is:

1. A fuel processor component for a propylene glycol fuel processor, comprising:
a housing having at least a first inlet and a second inlet and at least a first outlet and a second outlet,
a plurality of first plates each having a first side and a second side and a plurality of second plates each having a third side and a fourth side, wherein the plurality of first plates and the plurality of second plates are arranged as a stack in the housing,
wherein the stacked first and second plates form at least a plurality of first cavities and a plurality of second cavities, wherein the first inlet has fluid connection to the first outlet via the first cavities and the second inlet has fluid connection to the second outlet via the second cavities,
wherein the first side and the second side of each of the first plates are configured as evaporator surfaces,
wherein the third side of each second plate is configured as a hot gas side and the fourth side of each second plate is a flat surface, and
wherein each evaporator surface is opposite the flat surface and two hot gas sides are opposite one another.

2. The fuel processor component according to claim 1, wherein the first plates and/or the second plates have surface structuring, wherein the surface structuring comprises a pattern and/or channels having a distributor structure and a collection structure.

3. The fuel processor component according to claim 1, wherein a first number of the first and second plates is arranged in a given sequence, wherein the first number of the first and second plates forms a repeating unit.

4. The fuel processor component according to claim 3, wherein there is a multitude of third plates each having a fifth side and a sixth side arranged in the housing, wherein the third plates form an element of the repeating unit.

5. The fuel processor component according to claim 1, wherein the first side has structuring configured for a gas reaction and the second side is a cooling or evaporator side.

6. The fuel processor component according to claim 2, wherein the third side has the same surface structuring as the second side and the fourth side the same surface structuring as the first side.

7. The fuel processor component according to claim 1, wherein the fuel processor component is the evaporator, wherein at least a first side of a first plate is configured as evaporator and a second side for passage of hot gas.

8. The fuel processor component according to claim 4, having the plurality of first to sixth sides, wherein a repeating unit has the following sequence:
a first side, a second side, a fourth side, a third side, a third side, a fourth side, a first side, a second side, a fourth side, a third side, a third side, a fourth side, a sixth side, a fifth side, a fifth side, a sixth side.

9. The fuel processor component according to claim 1, wherein the fuel processor component is the heat exchanger, wherein at least one first side is configured for passage of a first gas and one second side for passage of a second gas.

10. The fuel processor component according to claim 9, wherein the heat exchanger is configured such that the first gas and the second gas can be guided through the fuel processor component in the same direction or in opposing directions.

11. The fuel processor component according to claim 1, wherein the fuel processor component is the water-gas shift reactor, wherein the first plate has a first side configured as a cooling side and a second side configured as a reaction side.

12. The fuel processor component according to claim 8, wherein every sixth side in a repeating unit is configured as a cooling side.

13. The fuel processor component according to claim 1, wherein the fuel processor component is a PrOx reactor,
wherein a first plate has a first side configured as a cooling side and a second side configured as a cooling side,
wherein a second plate has a third side configured as a reaction side and a fourth side configured as a gas feed side, wherein a third plate has a fifth side configured as a reaction side and a sixth side configured as an unstructured surface.

14. The fuel processor component according to claim 13, wherein a repeating unit has the following sequence:
first side, second side, sixth side, fifth side, third side, fourth side, fourth side, third side, fifth side, sixth side.

15. A propylene glycol fuel processor comprising a heat exchanger and a series connection of an evaporator, a reformer, a water-gas shift reactor and a PrOx reactor, wherein at least one of the fuel processor components is
a fuel processor component according to claim 1 configured as the evaporator, wherein at least a first side of a first plate is configured as evaporator and a second side for passage of hot gas,
a fuel processor component according to claim 1 configured as the heat exchanger, wherein at least one first side is configured for passage of a first gas and one second side for passage of a second gas,
a fuel processor component according to claim 1 configured as the water-gas shift reactor (R1), wherein the first plate has a first side configured as a cooling side and a second side configured as a reaction side and/or
a fuel processor component according to claim 1 configured as the PrOx reactor (R2), wherein a first plate has a first side configured as a cooling side and a second side configured as a cooling side,
wherein a second plate has a third side configured as a reaction side and a fourth side configured as a gas feed side,
wherein a third plate has a fifth side configured as a reaction side and a sixth side configured as an unstructured surface.

16. The propylene glycol fuel processor according to claim 15, wherein at least two of the fuel processor components are arranged one on top of the other such that the plate stacks of the at least two fuel processor components form a superstack.

17. The propylene glycol fuel processor according to claim 16, wherein a heat exchanger, a water-gas shift reactor and a PrOx reactor are arranged one on top of the other such that the plates thereof form a superstack,
wherein the water-gas shift reactor is arranged in a middle region of the superstack,
wherein the propylene glycol fuel processor is configured such that a first gas can flow successively through the heat exchanger, the water-gas shift reactor and the PrOx reactor.

* * * * *